United States Patent [19]

Shemano

[11] 4,041,165
[45] Aug. 9, 1977

[54] PHARMACEUTICALLY USEFUL NITROGEN CONTAINING HETEROCYCLIC DERIVATIVES

[75] Inventor: Irving Shemano, Cincinnati, Ohio

[73] Assignee: Richardson-Merrell Inc., Wilton, Conn.

[21] Appl. No.: 628,529

[22] Filed: Nov. 3, 1975

Related U.S. Application Data

[62] Division of Ser. No. 370,425, June 15, 1973, Pat. No. 3,937,835.

[51] Int. Cl.$^2$ .......................................... A61K 31/445
[52] U.S. Cl. .................................................. 424/267
[58] Field of Search ........................................ 424/267

[56]  References Cited
U.S. PATENT DOCUMENTS

| | | | |
|---|---|---|---|
| 3,531,489 | 9/1970 | Albrecht et al. | 424/267 |
| 3,592,819 | 7/1971 | Fleming et al. | 424/267 |
| 3,662,062 | 5/1972 | Krueger et al. | 424/267 |
| 3,673,191 | 6/1972 | Albrecht et al. | 424/267 |
| 3,692,907 | 9/1972 | Fleming et al. | 424/267 |
| 3,707,471 | 12/1972 | Albrecht et al. | 424/267 |

*Primary Examiner*—Jerome D. Goldberg
*Attorney, Agent, or Firm*—L. Ruth Hattan; Eugene O. Retter; George W. Rauchfuss, Jr.

[57]  ABSTRACT

Bis-basic substituted aromatic polycyclic compounds of the following structure are useful in treating conditions of delayed hypersensitivity:

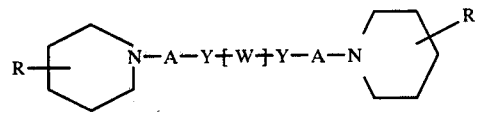

wherein [W] represents an aromatic polycyclic nucleus selected from fluoranthene, fluorene, fluoren-9-ol, fluoren-9-one, dibenzofuran, dibenzothiophene, carbazole, N-(lower)alkyl carbazole, xanthene, xanthone, thioxanthene, phenoxathiin, or anthraquinone; Y represents carbonyloxy, carbonylthio, oxygen, divalent sulfur or carbonyl with the provisos that when Y is carbonyloxy or carbonylthio, [W] is other than thioxanthene, phenoxathiin or anthraquinone, when Y is oxygen or divalent sulfur, [W] is other than thioxanthene or phenoxathiin, and when Y is carbonyl, [W] is other than fluoren-9-ol or anthraquinone; A represents a straight or branched alkylene chain of from 1 to 6 carbon atoms with the proviso that when Y is carbonyloxy or carbonylthio, A contains at least 2 straight chain carbon atoms, that is, an ethylene radical; R represents hydrogen, a straight or branched lower alkyl group of from 1 to 4 carbon atoms, phenyl or benzyl; and pharmaceutically useful acid addition salts.

8 Claims, No Drawings

PHARMACEUTICALLY USEFUL NITROGEN CONTAINING HETEROCYCLIC DERIVATIVES

This application is a divisional of copending application Ser. No. 370,425, filed June 15, 1973 now U.S. Pat. No. 3,937,835 issued Feb. 10, 1976.

FIELD OF INVENTION

This invention relates to the use of bis-basic substituted aromatic polycyclic derivatives wherein the basic substituents contain a piperidino radical for treating conditions of delayed hypersensitivity.

DESCRIPTION OF PRIOR ART

The following patents disclose bis-basic substituted aromatic polycyclic derivatives wherein the basic substituents contain a piperidino radical: U.S. Pat. No. 3,707,471 discloses bis-basic ether and thioether derivatives of fluoranthene. U.S. Pat. No. 3,592,819 and 3,692,907 discloses bis-basic ether and thioether derivatives of fluorene, fluoren-9-ol and fluoren-9-one. U.S. Pat. No. 3,673,191 discloses bis-basic ether and thioether derivatives of dibenzothiophene. Belgian Pat. No. 776,555 discloses bis-basic ether and thioether derivatives of xanthene and xanthone. Belgian Pat. No. 767,201, which is equivalent to pending U.S. application Ser. No. 37,312 now abandoned, discloses bis-basic ether derivatives of anthraquinone. U.S. Pat. No. 3,531,489 discloses bis-basic ester and thioester derivatives of fluoranthene. U.S. Pat. No. 3,647,860 discloses bis-basic ester derivatives of fluorene. U.S. Pat. No. 3,718,685 discloses bis-basic ester derivatives of fluoren-9-ol. U.S. Pat. No. 3,662,062 discloses bis-basic ester and thioester derivatives of fluoren-9-one. Great Britain Pat. No. 1,262,052, which is equivalent to pending U.S. application Ser. No. 833,717 now U.S. Pat. No. 3,867,409, discloses bis-basic ester derivatives of dibenzofuran. Great Britain Pat. No. 1,304,651 discloses bis-basic ketone derivatives of fluoranthene. Great Britain Pat. No. 1,286,755 discloses bis-basic ketone derivatives of fluorene and fluoren-9-one. Belgian patent 772,582, which is equivalent to pending U.S. application Ser. No. 72,171, discloses bis-basic ketone derivatives of dibenzofuran. Great Britain Pat. No. 1,292,567 discloses bis-basic ketoe derivatives of dibenzothiophene. Great Britain Pat. No. 1,312,534, which is equivalent to pending U.S. application Ser. No. 137,055 now U.S. Pat. No. 3,856,789, disclosed bis-basic ketone derivatives of thioxanthene. Belgian Pat. No. 776,535 which is equivalent to pending U.S. application Ser. No. 97,379 now U.S. Pat. No. 3,859,286, discloses bis-basic ketone derivatives of xanthene and xanthone. W. German Pat. No. 2,231,067, which is equivalent to pending U.S. application Ser. No. 158,122 now U.S. Pat. No. 3,808,206, discloses bis-basic ketone derivatives of phenoxathiin. Each of these disclosures describes the compounds therein a being useful as antiviral agents and do not suggest or render obvious the use of the compounds disclosed herein in the treatment of conditions of delayed hypersensitivity.

SUMMARY OF THE INVENTION

Bis-basic substituted aromatic polycyclic compounds of the following structure are useful in treating conditions of delayed hypersensitivity:

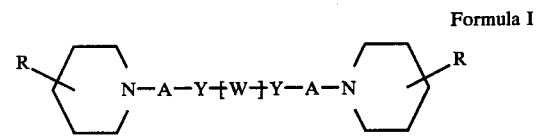

Formula I wherein [W] represents an aromatic polycyclic nucleus selected from fluoranthene, fluorene, fluoren-9-ol, fluoren-9-one, dibenzofuran, dibenzothiophene, carbazole, N-(lower)alkyl carbazole, xanthene, xanthone, thioxanthene, phenoxathiin, or anthraquinone; Y represents carbonyloxy, carbonylthio, oxygen, divalent sulfur or carbonyl with the provisos that when Y is carbonyloxy or carbonylthio, [W] is other than thioxanthene, phenoxathiin or anthraquinone, when Y is oxygen or divalent sulfur, [W] is other than thioxanthene or phenoxathiin, and when Y is carbonyl, [W] is other than fluoren-9-ol or anthraquinone; A represents a straight or branched alkylene chain of from 1 to 6 carbon atoms with the proviso that when Y is carbonyloxy or carbonylthio, A contains from 2 to 6 carbon atoms; R represents hydrogen, a straight or branched lower alkyl group of from 1 to 4 carbon atoms, phenyl or benzyl; and pharmaceutically acceptable acid addition salts.

DETAILED DESCRIPTION OF INVENTION

The compounds of this invention are bis-piperidinoalkylene derivatives of fluoranthene, as represented by the following general Formula II, bis-piperidinoalkylene derivatives of fluorene, fluoren-9-ol, fluoren-9-one, dibenzofuran, dibenzothiphene, carbazole, and N-(lower)alkyl carbazole, as represented by the following respective Formulas III-VII, bis-piperidinoalkylene derivatives of xanthene, xanthone, thioxanthene, phenoxathiin and anthraquinone, as represented by the following respective Formulas VIII-–XII.

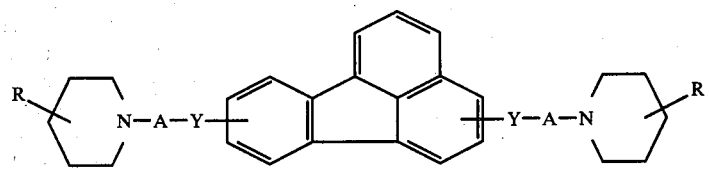

Formula II

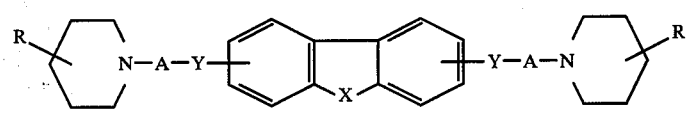

X —CH$_2$—   Formula III

Formula II

R—[piperidine]—N—A—Y—[fluoranthene]—Y—A—N—[piperidine]—R

Formula IV

R—[piperidine]—N—A—Y—[tricyclic with X]—Y—A—N—[piperidine]—R

| X | Formula |
|---|---|
| —CH(OH)— | IV |
| —C(=O)— | V |
| —O— | VI |
| —S— | VII |
| —N(R¹)— | VII |

Formula VIII

R—[piperidine]—N—A—Y—[biphenyl with Z, Z¹]—Y—A—N—[piperidine]—R

| Z | Z¹ | Formula |
|---|---|---|
| —CH₂— | O | VIII |
| —C(=O)— | O | IX |
| —CH₂— | S | X |
| —C(=O)— | S | XI |
| —C(=O)— | —C(=O)— | XII |

In the above general Formulas II to XII, R represents hydrogen, straight or branched lower alkyl group of from 1 to 4 carbon atoms, phenyl or benzyl, and may be attached to any one of the carbon atoms of the piperidino radical; A represents a straight or branched alkylene chain of from 1 to 6 carbon atoms with the proviso that when Y is carbonyloxy or carbonylthio, A contains at least 2 straight chain carbon atoms, that is, an ethylene group; Y represents carbonyloxy, carbonylthio, oxygen, divalent sulfur, or carbonyl with the following exceptions: in the compounds of general Formula IV, that is, bis-piperidinoalkylene derivatives of fluoren-9-ol, Y is other than carbonyl; in the compounds of general Formula X and XI, that is, bis-piperidinoalkylene derivatives of thioxanthene and phenoxathiin, Y is other than carbonyloxy, carbonylthio, oxygen or divalent sulfur; in the compounds of general Formula XII, Y is other than carbonyloxy, carbonylthio, or carbonyl; R¹ in the compounds of general Formula VII represents hydrogen or a lower alkyl group of from 1 to 4 carbon atoms.

In the compounds of general Formula II one of the basic substituents as represented by —Y—A—N—[piperidine]—R is attached to any one of the carbon atoms of the naphthalene portion of the tetracyclic nucleus, and the other such basic substituent is attached to any one of the carbon atoms of the benzenoid ring of the tetracyclic nucleus. In the compounds of general Formulas III to XII one of the basic substituents is attached to any one of the carbon atoms of one benzenoid ring of the tricyclic nucleus, and the other basic substituent is attached to the other such benzenoid ring.

Illustrative examples of straight or branched alkyl groups which R may represent in general Formulas I to XII are methyl, ethyl, n-propyl, isopropyl, n-butyl, isobutyl and tert-butyl.

Lower alkyl groups which R¹ may represent in the may represent in the compounds of general Formula VII are methyl, ethyl, n-propyl and n-butyl.

Illustrative examples of compounds of this invention are 2,7-bis(3-piperidinopropyl)-9-oxofluorene-2,7-dicarboxylate, 2,7-bis[4-(4-methylpiperidino)butyl]-9-oxofluorene2,5-dicarboxylate, 2,7-bis(2-piperidinoethyl)-9-oxofluorene2,7-dicarbothiolate, 2,7-bis(2-piperidinoethoxy)fluoren-9-one, 2,7-bis(3-piperidinopropylthio)-fluoren-9-one, 2,7-bis[5-(4-benzylpiperidino)valeryl]-fluoren-9-one, 2,5-bis(2-piperidinoacetyl)fluoren-9-one, bis(6-piperidinohexyl)fluorene-2,7-dicarboxylate, bis(3-piperidinopropyl)fluorene-2,7-dicarbothiolate, 2,7-bis(4-piperidinobutyoxy)fluorene, 2,5-bis[3-(4-ethylpiperidino)propoxy]fluorene, 1,7-bis(2-piperidinoethylthio)fluorene,2,7-bis(3-piperidinopropionyl)fluorene, 3,6-bis(3-piperidinobutyryl)fluorene, bis(2-piperidinoethyl)fluoren-9-ol-2,7-dicarboxylate, 2,7-bis(5-piperidinoopentoxy)fluoren-9-ol, bis(4-piperidinobutyl) dibenzofuran-2,6-dicarboxylate, bis(3-piperidinopropyl)dibenzofuran-2,8-dicarbothiolate, 2,6-bis(3-piperidinobutoxy)dibenzofuran, 2,8-bis(4-piperidinobutyryl)dibenzofuran, 2,8-bis(4-piperidinobutyryl)dibenzothiophene, 2,6bis[4-(4-phenylpiperidino)butoxy]dibenzothiphene, bis(3-piperidinopropyl)dibenzothiophene-2,8-dicarboxylate, 3,6-bis(4-piperidinobutyryl)-N-methylcarbazole, 2,8-bis(2-piperidinoethoxy)-N-ethylcarbazole, 3,6-bis(2-piperidinoacetyl)carbazole, bis(4-ethylpiperidinobutyl)-carbazole-3,6-dicarboxylate, bis(piperidinopentyl)xanthene-3,6-dicarboxylate, 2,7-bis(2-piperidinoethoxy)xanthene, 2,7-bis-(4-piperidinobutyryl)xanthen-9-one, 3,6-bis(3-piperidinopropylthio)xanthen-9-one, bis(3-piperidinoisobutyl)-9-oxo-xanthene-3,6-dicarboxylate, 2,8-bis(4-piperidinobutyryl)thioxanthene, 2,8-bis(2-piperidinoacetyl)thioxanthene, 2,8-bis(3-piperidinopropoxy)anthraquinone, 2,6-bis(2-piperidinoethoxy)anthraquinone, 2,7-bis(4-piperidinobutyryl)phenoxathiin, 2,8-bis[3-(4-ethylpiperidino)propionyl]phenoxathiin, bis(4-piperidinobutyl)fluoranthene-3,9-dicarboxylate, 4,8-bis(3-piperidinopropoxy)fluoranthene, 3,9-[4-(4-phenylpiperidono)butoxy]fluoranthene, 3,9-bis(4-piperidinobutyryl)fluoranthene, 3,9-bis(5-piperidinopentylthio)fluoranthene.

Pharmaceutically acceptable acid addition salts of the base compounds of this invention are those of any suitable inorganic or organic acid. Illustrative suitable inorganic acids are hydrochloric, hydrobromic, sulfuric, and phosphoric acids. Illustrative suitable organic acids are lower aliphatic hydrocarbon monocarboxylic acids, such as, glycolic or lactic acid; lower aliphatic lower alkoxyhydrocarbon monocarboxylic acids, such as, methoxyacetic or ethoxyacetic acids; lower aliphatic lower alkanoyl-hydrocarbon monocarboxylic acids, such as, pyruvic acid; lower aliphatic hydrocarbon dicarboxylic acids, such as malonic, succinic, methylsuccinic, glutaric, α-methylglutaric, β-methylglutaric, itaconic, maleic, citraconic, homocitraconic, or fumaric acid; lower aliphatic hydroxy hydrocarbon dicarboxylic acids, such as, malic or tartaric acid; lower aliphatic lower alkoxy-hydrocarbon dicarboxylic acids, such as, α,β-dimethoxysuccinic or ethoxymaleic acid; lower aliphatic hydrocarbon tricarboxylic acids, such as, aconitic or tricarballylic acid; lower aliphatic hydroxyhydrocarbon tricarboxylic acids, such as, citric acid. Additionally organic sulfonic acids, such as lower alkane sulfonic acids, for example, methanesulfonic or ethanesulfonic acid, or lower hydroxy-alkane sulfonic acids, for example, 2-hydroxyethane sulfonic acid or suitable. Particularly useful are pharmacologically acceptable acid addition salts with mineral acids, such as hydrochloric acid. Mono- or di-acid salts may be formed, and the salts may be hydrated, for example, monohydrate, or substantially anhydrous.

Introduction of an antigen, or a foreign substance, into an organism results in a specific immunological response changing the reactivity of the organism towards the antigen and substances closely resembling the antigen. This response is usually a heightened reactivity to the antigen. This heightened reactivity is due in part to the production of antibodies which can result in an Immediate hypersensitivity and in part to a cell-mediated immunity which can result in delayed hypersensitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to delayed hypersensitivity.

The type of substances which elicit delayed hypersensitivity are many and various. They may be organic chemicals, including drugs, simple chemical derivatives, or protein-containing antigens of micro-organisms, such as, bacteria, viruses, fungi or protozoa, or tissue antigens. Conditions of delayed hypersensitivity are associated with numerous pathological disorders, for example, contact hypersensitivity in the skin, rejection of tissue grafts or transplants, autoimmune diseases and certain infectious diseases. Such pathological disorders often involve, in addition to the cell-mediated delayed hypersensitivity responses, humoral antibody responses involving the production of antigen-specific antibodies. Generally, treatment of these disorders has been with immunosuppressive agents, such as, purine analogs, folic acid antagonists, alkylating agents and corticosteroids. Such agents have been found to be non-specific in their immunosuppressant effects, that is, they suppress both the humoral antibody and delayed (cell-mediated) hypersensitivity responses. [Drug Therapy, 1, No. 4, pp. 3–16 (1971)]. The compounds disclosed herein are unique in that they suppress only the delayed hypersensitivity response without concurrent suppression of the humoral immune response.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whoppingcough and leprosy; toxoids and vaccines, particularly diphtheria toxoid and smallpox vaccination; contact hypersensitivity in the skin, specifically from nickel salts, primrose or poison ivy, poison oak and paraphenylene diamine; rejection of tissue grafts and transplants; and autoimmune diseases, specifically rheumatoid arthritis, systemic lupus erythematosus, glomerular nephritis, rheumatic fever, ulcerative colitis, diabetes mellitus, pernicious anemia, coeliac disease, primary atypical pneumonia, Hashimoto's thyroditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reactions in vitro in the macrophage migration inhibition test (MMIT) and in vivo in the experimental allergic encephalomyelitis (EAE) test, which are well recognized tests for detecting agents or compounds effective in treating conditions of delayed hypersensitivity. *Immunology for Students of Medicine*, 3rd edition, 1970, F. A. Davis Company, pp. 498–500; Federation Proceedings 27, No. 1, pp. 3–15, (1968); Advances in Immunology 5, pp. 131–208 (1966).

As used herein, the term patient means warm blooded animals, particularly mammals and humans. The compounds disclosed herein may be administered to a patient orally, parenterally, or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.1 mg/kg (milligrams per kilogram) to about 200mg/kg of body weight of the patient per day, and preferably from about 1 mg/kg to 100 mg/kg of body weight of the patient per day, to achieve the desired effect. Unit doses can contain from about 5 mg to 1.0 g of a compound of this invention and may be administered, for example, from 1 to 4 times daily.

The compounds of this invention can be prepared by several methods. The bis-piperidinoalkylene ester and thioesters, that is compounds of general Formula I wherein Y represents carbonyloxy or carbonlythio can be prepared by the reaction of a compound of the formula Formula XIII

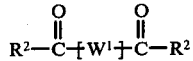

wherein $R^2$ is OH, halogen, such as, chlorine or bromine, or lower alkoxy, such as, methoxy or ethoxy and [$W^1$] represents fluoranthene, fluorene, fluoren-9-one, dibenzofuran, dibenzothiophene, carbazole, N-(lower-)alkyl carbazole, xanthene or xanthone; with a piperidinaoalkanol or piperidinoalkylthiol of the formula Formula XIV

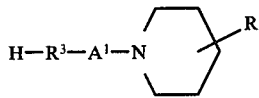

wherein $A^1$ is a straight or branched alkylene chain of from 2 to 6 carbon atoms; R represents hydrogen, lower alkyl of from 1 to 4 carbon atoms; R represents hydrogen, lower alkyl of from 1 to 4 carbon atoms, phenyl or benzyl and $R^3$ is oxygen or sulfur. The esterification can be achieved by allowing the compound of Formula XIII wherein $R^2$ is hydroxy, to react with the appropriate piperidinoalkanol or piperidinoalkylthiol in an inert solvent in the presence of a catalyst and employing general methods for removing water from the reaction site. Preferred solvents are chloroform, isopropyl alcohol, dioxane, and toluene. The reaction may be catalyzed by the use of mineral acids including hydrochloric, sulfuric or certain organic acids such as p-toluenesulfonic acid. Methods whereby water can be removed from the reaction include the use of water scavengers such as the carbodiimides or by the azeotropic removal of water. The reaction will proceed at temperatures ranging from 50°–150° C. over a period of 6 to 72 hours depending upon the solvent and catalyst.

Preferably, the esterification can be achieved by allowing the acid halide, where $R^2$ in the above Formula XIII is halogen, to react with the appropriate piperidinoalkanol or piperidinoalkylthiol. The esters and thioesters of this invention can be produced in a variety of inert solvents over a wide range of temperatures and reaction time. The solvents of choice include chloroform, dioxane, tetrahydrofuran, and the aromatic solvents such as benzene and toluene. In chloroform, the reaction is generally complete within one hour at the reflux temperature of the solvent, although the reaction time can range from 15 minutes to 3 days.

The bis-basic ester and thioester derivatives of general Formula I may also be prepared by a transesterification reaction in which a (lower)alkoxy ester, that is, a compound of Formula XIII wherein $R^2$ is, for example, methoxy or ethoxy, is reacted with the appropriate piperidinoalkanol or piperidinoalkylthiol under suitable conditions. This type of reaction is catalyzed by alkaline or acid catalysts and is reversible. The basic esters may be obtained by causing the equilibrium to be shifted by removing the piperidinoalkanol or piperidinoalkythiol component or by employing a large excess of the piperidinoalkanol or piperidinoalkylthiol. Preferably, the reaction is carried out by removing the alkanol or alkythiol component with the use of an alkaline catalyst. The alkanol or alkylthiol component may be removed by direct distillation or distillation with a suitable solvent. Suitable alkaline catalysts are alkali metals, such as, sodium or potassium; alkali lower alkoxides, such as, sodium methoxide or sodium ethoxide; or alkali amides such as lithium or sodium amide. Suitable solvents are those forming an azeotropic distillation mixture with the alkanol or alkylthiol component, for example, benzene or toluene, or a solvent which boils sufficiently higher than the alkanol or alkylthiol to permit its removal by distillation at a temperature below that of the boiling range of the solvent.

The bis-piperidinoester and thioester derivatives of general Formula 1 wherein [W] represents fluoren-9-ol or fluorene may be prepared by the reduction of the corresponding fluoren-9-one compound. The reduction of the fluoren-9-one derivatives can be carried out either chemically or by hydrogenation in the presence of a catalyst. Hydrogenation of the fluorenone bis esters takes place in a stepwise fashion. Thus, at room temperature and low pressure, one equivalent of hydrogen is rapidly absorbed to give the fluorenol derivative. Subsequent uptake of hydrogen is much slower so that if the fluorene derivative is desired, the reaction mixture should be heated to shorten the reaction periods. The hydrogenation can be carried out in any of a variety of solvents such as water, alcohols such as ethanol or methanol, dimethylformamide, or mixtures of these solvents. The fluorene compound is hydrogenated in the acid addition salt form. Hydrogenation catalysts such as palladium or platinum, supported or unsupported, may be used in this hydrogenation.

The fluorenol esters of this invention may be prepared by the chemical reduction of the corresponding base form of the fluorene derivatives such as with sodium borohydride, lithium borohydride, and the like, at 0°– 100° C for 10 minutes to 4 hours in a suitable solvent such as water, ethanol and the like. The fluorenone bis-basic esters and thioesters may be added to the borohydide reagent, either as the base dissolved in an organic solvent such as alcohols, or as the salt in an aqueous or aqueous-alcoholic solution. In the latter case, an excess of borohydride reagent should be used to compensate for reagent consumed by neutralization of the salt.

Additional methods for the preparation of bis-basic ester and/or thioester derivatives of fluoroanthene, fluorene, fluoren-9-ol, and fluoren-9-one are set forth respectively in U.S. Pat. No. 3,531,489, 3,647,860, 3,718,685 and 3,662,062, and the appropriate portions of each patent are incorporated herein by reference thereto.

The compounds of general Formula 1 wherein Y is oxygen or divalent sulfur, that is, bis-piperidinoalkylene ether and thioether derivatives may be prepared by the reaction of one equivalent of a diol or dithiol derivative of the formula HR⁴ + W² + R⁴H   Formula XV wherein R⁴ represents oxygen or divalent sulfur; and [W²] represents fluoranthene, fluorene, fluoren-9-ol, fluoren-9-one, dibenzofuran, dibenzothiophene, carbazole, N-(lower)alkyl carbazole, xanthene, xanthone, or anthraquinone; with two equivalents of a piperidinoalkylhalide of the formula Formula XVI

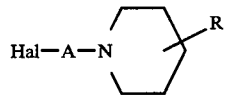

wherein Hal represents chlorine, bromine or iodine; A is a straight or branched alkylene chain of from 1 to 6 carbon atoms; and R is hydrogen, lower alkyl of from 1 to 4 carbon atoms, phenyl or benzyl; in the presence of a base. Typical piperidinoalkyl halides are, for example, 2-piperidinoethylchloride, 3-piperidinopropylbromide, 3-piperidinoisobutylchloride, and 3-(4-methylpiperidino)propylchloride.

Alternatively, the bis-piperidinoalkylene ether and thioether derivatives of general Formula 1 may be prepared by the reaction of a bis-ω-haloalkylether or thioether derivative of the formula Hal-A-R⁴ + W² + R⁴-A-Hal   Formula XVII wherein Hal, A, R⁴ and [W²] have the meanings defined hereinabove with piperidine or an appropriately substituted piperidine. The bis-ω-haloalkyl ether and thioether derivatives of Formula XVII are obtained by the reaction of a diol or dithiol derivative of [W²] with a haloalkylhalo, that is Hal-A-Hac wherein Hal and A have the meanings defined hereinabove, in the presence of a base.

Suitable bases for the above described reaction are sodium methoxide, sodium hydride, sodium amide, sodium hydroxide, and potassium hydroxide. Suitable solvents include aromatic hydrocarbons, such as benzene, toluene and xylene; halogenated aromatics, such as, chlorobenzene; aprotic solvents, such as, N,N-dimethylformamide, N,N-dimethylacetamide, and dimethylsulfoxide; alcohols, such as, ethanol or isopropyl alcohol; ketones, such as, acetone; ethers, such as, tetrahydrofuran or dioxane; water; or mixtures of these solvents.

When either sodium methoxide, sodium amide or sodium hydride, for example, is used as the base, the reaction is carried out in an anhydrous medium, such as anhydrous toluene or chlorobenzene. About 2.5 equivalents of the base is added to a suspension of a diol or dithiol derivative of Formula XV, in the anhydrous solvent, and the mixture is heated. In the case where sodium methoxide is used, the methanol formed may be removed advantageously by azeotropic distillation. About 2.5 equivalents of the halide, either a piperidinoalkylhalide or a haloalkylhalo derivative is added, and the mixture heated to reflux for a period which may vary from about 4 to 24 hours. The products are isolated by customary procedures.

In the method where an alkali hydroxide, such as potassium hydroxide is used as the base, two different procedures may be used. In the one procedure a 25 to 50 percent aqueous solution of the alkali hydroxide (about 2.5 equivalents) is added to a suspension of a diol or dithiol derivative of Formula XV in a suitable aromatic solvent, for example xylene. This mixture is then heated to boiling, stirring being optional, and the water removed by azeotropic distillation. The reaction mixture, now being essentially anhydrous, is treated with about 2.5 equivalents of either a piperidinoalkylhalide or a haloalkylhalo derivative. In the other procedure the reaction is carried out in a heterogenous medium of water and an aromatic hydrocarbon, such as, toluene or xylene. For example, one equivalent of a diol or dithiol derivative of Formula XV is suspended in the aromatic hydrocarbon. To this suspension is added about 2.5 equivalents of a hydrohalide salt of a piperidinoalkylhalide derivative or a haloalkylhalo derivative in a minimum volume of water after which a 25 to 50% solution of the alkali hydroxide (about 5 equivalents when using a piperidinoalkylhalide derivative and about 2 equivalents when using a haloalkylhalo derivative) is added with efficient stirring. This mixture is heated to reflux for about 6 to 24 hours, and the product is isolated from the hydrocarbon layer.

The reaction between the bis-ω-haloalkylether or thioether derivative of Formula XVII and piperidine may be carried out under a variety of conditions. For example, the compound of Formula XVII may be heated together with a large excess of the piperidine, the excess piperidine serving as both the reaction medium and the hydrohalide acceptor. Or, 1 equivalent of the bis(ω-haloalkyl)ether or thioether, and 4 equivalents of the piperidine may be heated together in one of a number of different types of solvents, for example, in aromatic solvents, such as, benzene, toluene, xylene, or chlorobenzene; or lower molecular weight alcohols, such as, methanol, ethanol or isopropyl alcohol; or lower molecular weight ketones, such as, acetone or methyl ethyl ketone. The reaction between the halo compound and the piperidine is usually promoted by the addition of either sodium or potassium iodide, the iodide being used in either catalytic or stoichiometric amounts. In some cases, it may be advantageous to use only 2 equivalents of the piperidine for each equivalent of the bis-ω-haloalkylether or thioether, an excess of either powdered potassium carbonate or sodium carbonate being used as the hydrohalide acceptor.

Additional methods for the preparation of bis-piperidinoalkylene ether and thioether derivatives of fluoranthene are set forth in U.S. Pat. No. 3,707,471; of fluorene, fluoren-9-ol, and fluoren-9-one are set forth in U.S. Pat. Nos. 3,592,819 and 3,692,907; of dibenzothiophene are set forth in U.S. Pat. No. 3,673,191; of xanthene and xanthone are set forth in Belgian Pat. No. 776,555; of 2,6- and 2,7-bis-piperidinoalkylene ether anthraquinone derivatives are set forth in Belgian Pat. No. 767,201; and the appropriate portions of each disclosure are incorporated herein by reference thereto. The additional methods set forth in these disclosures may be appropriately applied to the preparation of bis-piperidinoalkylene ether and thioether derivatives of dibenzofuran, carbazole and anthraquinone.

The compounds of general Formula I wherein Y is carbonyl, and [W] represents fluoranthene, fluorene, dibenzofuran, dibenzothiophene, carbazole, N(lower)alkyl carbazole, xanthene, thioxanthene, or phenoxathiin, may be prepared by an amination reaction of a bis-ω-haloalkanoyl derivative of the formula

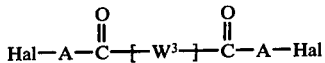
Formula XVIII wherein Hal is chlorine, bromine or iodine; A is a straight or branched alkylene chain of from 1 to 6 carbon atoms; and [$W^3$] represents fluoranthene, fluorene, dibenzofuran, dibenzothiophene, carbazole, N-(lower)alkyl carbazole, xanthene, thioxanthene or phenoxathiin; with piperidine or an appropriately substituted piperidine.

The amination reaction may be carried out under a variety of conditions. For example, a compound of Formula XVIII may be heated together with a large excess of the piperidine, the excess piperidine serving as the reaction medium and the hydrohalide acceptor. Or, one equivalent of a compound of Formula XVIII and four equivalents of the piperidine, may be heated together in one of a number of different types of solvents, for example, in aromatic solvents, such as, benzene, toluene, or xylene; ethers, such as, tetrahydrofuran, or dioxane; ketones, such as, acetone or butanone; aprotic solvents, such as, N,N-dimethylformamide, N,N-dimethylacetamide, or dimethyl sulfoxide; or mixtures of these solvents with water. The reaction between a compound of Formula XVIII wherein Hal is Cl and the piperidine, is frequently promoted by the addition of either sodium iodide or potassium iodide, the iodide being used in either catalytic or stoichiometric amounts. In some cases, it may be advantageous to use only two equivalents of the piperidine for each equivalent of the bis-ω-haloalkanoyl derivative, an excess of an inorganic base, such as, powdered sodium carbonate or potassium carbonate being used as the hydrohalide acceptor. The reaction will proceed normally in 12 hours to two weeks at temperatures of from −30° to 150° C.

Alternatively, the amination reaction may be carried out on a derivative of a compound of Formula XVIII, such as, the bis-ketal derivative that may be prepared by allowing the bis-ω-haloalkanoyl derivative and an excess of ethyl orthoformate to react in the presence of an acid catalyst such as hydrochloric acid for several days in a polar solvent such as ethanol or tetrahydrofuran.

The bis-ω-haloalkanoyl derivatives of Formula XVIII can be prepared by a Friedel-Crafts acylation reaction of an appropriate aromatic polycyclic compound as represented by [$W^3$]. Suitable acylating agents which may be used are, for example, chloroacetyl chloride, bromoacetyl bromide, 3-chloropropionyl chloride, 4-chlorobutyryl chloride, 5-chloro-4-methylvaleryl chloride and 4-chloro-3-ethylbutyryl chloride.

The acylation reaction may be carried out in a variety of solvents and under catalysis of a variety of Lewis acids. The temperature and duration of the reaction may be varied to allow for optimum reaction conditions. A preferred procedure is to combine one equivalent of an appropriate aromatic polycyclic compound as represented by [$W^3$] with 2.5 equivalents of an acylating agent in methylene chloride followed by portionwise addition of aluminum chloride. The temperature of the reaction is maintained below zero degrees with continuous stirring. After the additions are complete the temperature may be elevated to 25°-40° C for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic polycyclic compound and Lewis acid. The more reactive halogen derivative, that is, the bis-ω-iodoalkanoyl derivative, may be prepared from the corresponding bis-chloro derivative using a halogen exchange reaction under the conditions generally employed in the Conant-Finkelstein reaction.

The acylation reaction described above results in bis-ω-haloalkanoyl derivatives of Formula XVIII wherein the position of substitution on the various aromatic polycyclic compounds is the following: 3,9-bis-ω-haloalkanoylfluoranthene; 2,7-bis-ω-haloalkanoylfluorene; 2,6- and 2,8-bis-ω-haloalkanoyldibenzofuran; 2,6- and 2,8-bis-ω-haloalkanoyldibenzothiophene; 3,6-bis-ω-haloalkanoylcarbazole; 2,7-bis-ω-haloalkanoylxanthene; 2,7-bis-ω-haloalkanoylthioxanthene; and 2,7- and 2,8-bis-ω-haloalkanoylphenoxathiin.

The bis-piperidinoalkanoyl derivatives of general Formula I wherein [W] represents fluoranthene, fluorene, dibenzofuran, dibenzothiophene, carbazole, or N-(lower)alkylcarbazole, and A is an alkylene chain of from 3 to 6 carbon atoms may be prepared by the reaction of a dinitrile derivative of the formula

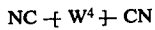
Formula XIX wherein [$W^4$] represents fluoranthene, fluorene, dibenzofuran, dibenzothiophene, carbazole or N-(lower)alkylcarbazole with a Grignard reagent of the formula

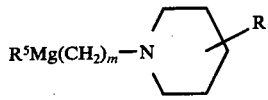
Formula XX wherein $R^5$ is bromine or chlorine; m is an integer of from 3 to 6; and R is hydrogen, lower alkyl of from 1 to 4 carbon atoms, phenyl or benzyl. The reaction will proceed in from 1 to 24 hours at a temperature ranging from room temperature to about 80° C. The Grignard reagent may be prepared by reacting magnesium and piperidinoalkyl $C_{3-6}$-halide wherein the halide is bromine or chlorine; a preferred solvent for this reaction is tetrahydrofuran. The dinitrile derivatives of Formula XIX may be prepared from known diamines by a Sandmeyer reaction on the tetrazonium salts or from known dicarboxylic acid derivatives by dehydration of the corresponding amides by standard procedures.

The bis-piperidinoalkanoyl derivatives of general Formula I wherein [W] is xanthene, thioxanthene or phenoxathiin, and wherein A is an alkylene chain of from 3 to 6 carbon atoms may be prepared by the reaction of a Grignard reagent of the above Formula XX with a bis-amide derivative of the formula

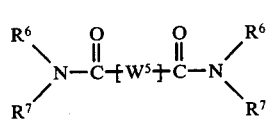
Formula XXI wherein [$W^5$] represents xanthene, thioxanthene or phenoxathiin, and $R^6$ and $R^7$ represent hydrogen or lower alkyl, or NR⁶R⁷ together form a saturated monocyclic heterocyclic group, such as, pyrrolidino or piperidino. The addition of the Grignard reagent is carried out at low temperatures ranging from −70° C to 0° C, and the reaction mixture is then warmed to 0° to 80° C for 1 to 24 hours. The bis-amide derivatives may be prepared by generally known procedures from the corresponding bis-acids.

The bis-piperidinopropionyl derivatives of general Formula I wherein [W] represents fluoranthene, fluorene, dibenzofuran, dibenzothiophene, xanthene, thioxanthene or phenoxathiin may be prepared by a Mannich reaction of a bis-acetyl derivative of the formula

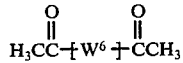

Formula XXII wherein [W⁶] represents fluoranthene, fluorene, dibenzofuran, dibenzothiophene, xanthene, thioxanthene or phenoxathiin with piperidine or an appropriately substituted piperidine in the presence of formaldehyde. By combining one equivalent of a compound of Formula XXII and two or more equivalents of the piperidine with three or more equivalents of formaldehyde the reaction will proceed in from a few minutes to 24 hours in solvents such as water, acetic acid, ethanol, butanol, dioxane, and tetrahydrofuran and at temperatures equivalent to the reflux temperature of the solvent. In this reaction either of two sources of formaldehyde may be employed. When formalin is used the reaction may be conducted with a suspension of a compound of Formula XXII or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The piperidine employed in this reaction may be added to the reaction medium as the hydrochloride salt or as the base form with subsequent in situ formation of the hydrochloride salt by the addition of hydrochloric acid.

The bis-acetyl derivatives of Formula XXII may be prepared by a Friedel-Crafts acylation reaction on fluoranthene, fluorene, dibenzofuran, dibenzothiophene, xanthene, thioxanthene, or phenoxathiin, or by a reaction of a bis-acid chloride derivative of the same aromatic polycyclic compounds with dimethyl-cadmium, which can be prepared from methyl Grignard and cadmium chloride. The bis-acid chlorides can be prepared by conventional procedures.

The bis-piperidinoalkanoyl derivatives of fluoren-9-one and xanthone, that is, compounds of general Formula I wherein Y is a carbonyl and [W] represents fluoren-9-one or xanthone can be prepared by oxidation of the corresponding fluorene or xanthene bis-piperidinoalkanoyl derivatives, the preparations of which are described hereinabove. This oxidation reaction may be carried out using dichromate anion such as sodium dichromate or potassium dichromate as the oxidizing agent. The reaction will proceed in from 15 minutes to 6 hours at a temperature of from 80° to 120° C. The amount of oxidizing agent is limited to the stoichiometric quantity required for oxidation of the 9-methylene group of the fluorene or xanthene derivative.

Suitable solvents for this conversion are, for example, water, acetic acid and tert-butyl alcohol, or combinations of these solvents. For example, by combining three moles of a bis-piperidinoalkanoyl fluorene or xanthene derivative of general Formula I, wherein Y is carbonyl, and [W] is fluorene or xanthene, dissolved in acetic acid with four moles of sodium dichromate and refluxing the mixture for 1 to 3 hours, the corresponding fluoren-9-one and xanthone derivatives are obtained.

EXAMPLE 1

Bis(3-piperidinopropyl)fluoranthene-3,8-dicarboxylate dihydrochloride

To 400 ml of chloroform is added 15.0 g (0.046 mole) of fluoranthene-3,8-dicarbonyl chloride and 13.3 g (0.093 mole) of 3-piperidinopropanol and the resulting solution is heated to reflux. After a short time, the product separates from the refluxing reaction mixture and after refluxing for a total time of 3 hours a yellow product is separated by filtration and is crystallized twice from methanol-ethyl acetate to give bis(3-piperidinopropyl)fluoranthene-3,8-dicarboxylate dihydrochloride, M.P. 258°–260° C.

EXAMPLE 2

Bis(3-piperidinopropyl)-9-oxofluorene-2,7-dicarboxylate dihydrochloride

A suspension of 30.5 g (0.12 mole) of fluoren-9-one-2,7-dicarbonyl chloride in 1 liter of dry chloroform free from ethanol is stirred and treated with 37.5 g (0.26 mole) of 3-piperidino-1-propanol resulting in a mildly exothermic reaction. The resulting mixture is stirred and refluxed for two hours, cooled to room temperature, filtered, and the filtrate washed three times with 250 ml portions of saturated sodium bicarbonate solution. The chloroform solution is then washed with water and saturated sodium chloride solution, dried over anhydrous sodium sulfate, and filtered. Most of the solvent is removed from the filtrate on a steam bath under vacuum, and the residue is dissolved in butanone. The solution is made acidic to Congo Red with ethereal HCl causing the product to precipitate as a yellow crystalline solid. The solid is filtered, recrystallized from butanone-methanol and dried to give bis(3-piperidinopropyl)-9-oxofluorene-2,7-dicarboxylate dihydrochloride, M.P. 293°–295° C (dec.).

EXAMPLE 3

Bis(3-piperidinopropyl)fluorene-2,7-dicarboxylate dihydrochloride

A solution of 20.0 g (0.04 mole) of bis(3-piperidinopropyl)-9-oxofluorene:2,7-dicarboxylate dihydrochloride in water to make a total volume of 240 ml is hydrogenated over 8.0 g of 10% palladium on charcoal for 2 days at 53° C on a Parr hydrogenation apparatus. The mixture is decanted from the catalyst, filtered through filter aid, treated with charcoal and refiltered. The solution is made basic to phenolphthalein with 20% sodium hydroxide and is extracted three times with CHCl₃. The combined extracts are washed twice with water, dried over anhydrous sodium sulfate and filtered. The filtrate is made acidic to Congo Red with ethereal HCl. Most of the solvent is removed on a steam bath under vacuum, and the resulting solid is recrystallized from methanol-ether and from absolute ethanol and vacuum dried to give bis(3-piperidinopropyl)fluorene-2,7-dicarboxylate dihydrochloride.

EXAMPLE 4

Bis(3-piperidinopropyl) 9-hydroxyfluorene-2,7-dicarboxylate dihydrochloride hydrate A solution of 10.3 g (0.020 mole) of bis(3-piperidinopropyl)-9-oxofluorene-2,7-dicarboxylate dihydrochloride in 350 ml of warm water is cooled to room temperature and added to 3 g (0.079 mole) of $NaBH_4$ in 15 ml of water with swirling. The resulting product is extracted 5 times with ether, and the combined ether extracts are washed with water, then with NaCl solution, and dried over anhydrous $MgSO_4$. The mixture is filtered, the filtrate treated with ethereal HCl and most of the solvent distilled off. The residue is dissolved in 50 ml of hot ethanol, filtered through filter aid and the filtrate refrigerated. The crystallized solid is filtered off and is recrystallized twice from ethanol to give bis(3-piperidinopropyl) 9-hydroxyfluorene-2,7-dicarboxylate dihydrochloride hydrate.

EXAMPLE 5

Bis(3-piperidinopropyl)dibenzofuran-2,8-dicarboxylate dihydrochloride monohydrate A solution of 12.8 g (0.44 mole) of dibenzofuran-2,8-dicarbonyl chloride and 12.6 g (0.088 mole) of 3-piperidinopropanol in 1 liter of chloroform is refluxed for 4 hours. Upon dilution with diethyl ether, the product is collected and crystallized from ethanol, to give bis(3-piperidinopropyl)dibenzofuran-2,8-dicarboxylate dihydrochloride monohydrate, M.P. 252°–253° C.

EXAMPLE 6

Bis(3-piperidinopropyl)dibenzothiophene-2,6-(and 2,8)-dicarboxylate dihydrochloride monohydrate A solution of 12.0 g (0.038 mole) of a mixture of dibenzothiophene-2,6-(and 2,8)-dicarbonyl chloride and 11.4 g (0.08 mole) of 3-piperidinopropanol in 500 ml of chloroform is heated at reflux for 24 hours. The solid which separates is treated with 25% aqueous sodium carbonate and the free base which results is extracted with ether, dried over anhydrous magnesium sulfate and treated with ethereal hydrogen chloride. The dihydrochloride salt is recrystallized several times from methanol-ethyl acetate to yield bis(3-piperidinopropyl)-dibenzothiophene-2,6-(and 2,8-)dicarboxylate dihydrochloride monohydrate, consisting of approximately 75% of the 2,6-isomer and 25% of the 2,8-isomer, M.P. 248°–256° C.

EXAMPLE 7

Bis(3-piperidinopropyl)-9-ethylcarbazole-3,6-dicarboxylate dihydrochloride

To 250 ml of isopropyl alcohol is added one equivalent of 9-ethylcarbazole-3,6-dicarboxylic acid, 2 equivalents of 3-piperidinopropylchloride, and a catalytic amount of benzyltrimethylammonium chloride. The mixture is heated to reflux for 2 hours. Upon cooling a solid forms which is collected, washed with ether, dried and dissolved in water. The aqueous solution is made basic with saturated sodium bicarbonate, and the product is extracted with ether. The ether solution is washed with water, dried, and acidified with ethereal HCl. The resulting precipitate is recrystallized from methanol-butanone to give bis(3-piperidinopropyl)-9-ethylcarbazole-3,6-dicarboxylate dihydrochloride.

EXAMPLE 8

Bis(3-piperidinopropyl)xanthone-2,7-dicarboxylate dihydrochloride

To 14.2 g (0.05 mole) of xanthone-2,7-dicarboxylic acid is added 150 ml (2.1 mole) of thionyl chloride and 100 ml of dry tetrahydrofuran. The resulting solution is refluxed for three hours after which the solvent and excess thionyl chloride are removed at reduced pressure on a steam bath. The residue is dissolved in 500 ml of dry methylene chloride, treated with activated charcoal and filtered. To the filtrate, containing xanthone-2,7-dicarboxylic acid chloride, is added 18.6 g (0.13 mole) of 3-piperidinopropanol. The resulting mixture is refluxed 1.5 hours and let stand for three days. The solvent is removed, and the residue is dissolved in dilute hydrochloric acid and washed with methylene chloride. The aqueous layer is made basic with 15% sodium carbonate solution and extracted with methylene chloride. This solution is washed with dilute sodium carbonate solution and water and then dried over anhydrous magnesium sulfate. Upon filtering, the solvent is removed under reduced pressure and the residue dissolved in isopropyl alcohol and converted to the dihydrochloride with ethanolic-HCl. The product is precipitated with diethyl ether, filtered and purified from isopropanol-methanol to give bis(3-piperidinopropyl)xanthone-2,7-dicarboxylate dihydrochloride.

EXAMPLE 9

Bis(3-piperidinopropyl)xanthene-2,7-dicarboxylate dihydrochloride

When in Example 8, xanthene-2,7-dicarboxylic acid is substituted for xanthone-2,7-dicarboxylic acid, bis(3-piperidinopropyl)xanthene-2,7-dicarboxylate dihydrochloride is obtained.

EXAMPLE 10

Bis(2-piperidinoethyl) 9-oxofluorene-2,7-dicarbothiolate dihydrochloride 12.2 grams (0.04 mole) 9-oxofluorene-2,7-dicarbonyl chloride and 15.4 grams (0.085 mole) of piperidinoethanethiol hydrochloride are mixed in 500 ml of dried chloroform. The reactants are refluxed with stirring for two hours and allowed to cool to room temperature. The mixture is diluted with 180 ml of saturated sodium bicarbonate solution and 165 ml water. After thorough mixing, the layers are separated and the aqueous layer is extracted twice with chloroform. The combined chloroform extracts are washed with water and saturated sodium chloride and dried over $MgSO_4$. After filtering the $MgSO_4$, the filtrate is acidified to Congo Red paper with ethereal HCl. Upon concentration and cooling, a yellow crystalline precipitate of bis(2-piperidinoethyl) 9-oxofluorene-2,7-dicarbothiolate dihydrochloride separates. It is filtered off, washed with ether, dried and recrystallized from methanol M.P. 265°–7° C.

EXAMPLE 11

When in the procedure of Example 10, fluoranthene-3,9-dicarbonyl chloride or dibenzofuran-2,8-dicarbonyl chloride is substituted for 9-oxofluorene-2,7-dicarbonyl the following respective products are obtained:

Bis(2-piperidinoethyl)fluoranthene-3,9-dicarbothiolate dihydrochloride, and
Bis(2-piperidinoethyl)dibenzofuran-2,8-dicarbothiolate dihydrochloride.

EXAMPLE 12

3,9-Bis(3-piperidinopropoxy)fluoranthene

To 200 ml of water containing 16.0 g (0.4 mole) of sodium hydroxide and 15.7 g (0.067 mole) of 3,9-dihydroxyfluoranthene are added 200 ml of toluene and 29.8 (0.15 mole) of 3-piperidinopropyl chloride hydrochloride and the heterogeneous reaction mixture is stirred at reflux for 24 hours. After cooling, the organic layer is washed with water, dried over magnesium sulfate, and concentrated in vacuo. The residue is crystallized from ether to give 3,9-bis(3-piperidinopropoxy)fluoroanthene, M.P. 92°–93° C.

EXAMPLE 13

2,7-Bis(4-piperidinobutoxy)fluorene dihydrochloride

A solution of 13.1 g (0.075 mole) of 4-piperidinobutyl chloride in 100 ml of toluene is added to a mixture of 4.9 g (0.025 mole) of 2,7-dihydroxyfluorene and 2.7 g (0.05 mole) of sodium methoxide in 200 ml of toluene. The mixture is refluxed with stirring for 12 hours. Upon cooling, the mixture is filtered to remove the precipitated sodium chloride. The toluene solution is washed with water, then with sodium chloride solution and dried over anhydrous magnesium sulfate. This mixture is filtered and the filtrate acidified to Congo Red with ethereal HCl. The precipitate is collected and recrystallized from butanone-methanol to give 2,7-bis(4-piperidinobutoxy)fluorene dihydrochloride.

EXAMPLE 14

2,7-Bis(2-piperidinoethoxy)fluoren-9-one dihydrochloride

A mixture of 5.3 g (0.025 mole) of 2,7-dihydroxyfluoren-9-one in 100 ml of toluene, 16.2 g (0.088 mole) of 2-piperidinoethylchloride hydrochloride and 5.0 g (0.125 mole) of sodium hydroxide in 40 ml of water is heated at reflux for 15 hours with stirring. Upon cooling, the layers are separated. The toluene layer is washed with water and saturated sodium chloride solution, dried over anhydrous magnesium sulfate and filtered. The filtrate is acidified to Congo Red with ethereal HCl, and the resulting precipitate is collected, washed with ether and recrystallized from butanone-methanol to give 2,7-bis(2-piperidinoethoxy)fluoren-9-one dihydrochloride, M.P. 304°–306° C.

EXAMPLE 15

2,8-Bis(3-piperidinopropoxy)dibenzofuran dihydrochloride

To 200 ml of water containing 13.0 g (0.33 mole) of sodium hydroxide and 12.0 g (0.06 mole) of 2,8-dihydroxydibenzofuran are added 250 ml of toluene and 29.7 g (0.15 mole) of 3-piperidinopropyl chloride hydrochloride, and the heterogeneous reaction mixture is heated to reflux with stirring for 24 hours. When cool, the organic layer is washed with water, dried over magnesium sulfate then concentrated in vacuo. The remaining oily residue is dissolved in ether and treated with ethereal HCl to give the desired product which is recrystallized twice from methanol-ethyl acetate yielding 2,8-bis(3-piperidinopropoxy(dibenzofuran dihydrochloride, M.P. 245°–246.5° C.

EXAMPLE 16

2,8-Bis(3-piperidinopropoxy)dibenzothiophene dihydrochloride

To 200 ml of water containing 12.0 g (0.3 mole) of sodium hydroxide and 8.5 g (0.039 mole) of 2,8-dihydroxydibenzothiophene are added 200 ml of toluene and 19.8 g (0.1 mole) of 3-piperidinopropyl chloride hydrochloride, and the heterogeneous reaction mixture is stirred and heated to reflux for 16 hours. After cooling, the organic layer is washed with water, dried over magnesium sulfate, and concentrated in vacuo. The free base is chromatographed on alumina, using chloroform as the eluant. After removing the chloroform from the fraction collected, the oily residue is dissolved in ether and treated with ethereal hydrogen chloride. The resulting solid is purified by two recrystallizations from methanol-butanone to give 2,7-bis(3-piperidinopropoxy)dibenzothiophene dihydrochloride, M.P. 240°–242° C.

EXAMPLE 17

N-Ethyl-3,6-bis(2-piperidinoethoxy)carbazole hydrochloride

A mixture of 15.5 g (0.05 mole) of N-ethyl-3,6-carbazolediol diacetate, 18.4 g (0.1 mole) of 2-piperidinoethylchloride hydrochloride, 10.8 g (0.2 mole) of sodium methoxide and 400 ml of chlorobenzene is refluxed for 24 hours. Upon cooling, the reaction mixture is filtered, and the filtrate is washed with several portions of water, dried over anhydrous magnesium sulfate, diluted with ether and acidified with ethereal HCl. The resulting precipitate is collected and recrystallized from methanol-ethyl acetate to give N-ethyl-3,6-bis(2-piperidinoethoxy)carbazole dihydrochloride, M.P. 248°–250° C.

EXAMPLE 18

2,7-Bis(2-piperidinoethoxy)xanthene

To 20 g (0.093 mole) of 2,7-dihydroxyxanthene in 350 ml of chlorobenzene are added 16.5 g (0.3 mole) of sodium methoxide and 60 ml of methanol. The reaction mixture is stirred and heated during which time the methanol is removed by distillation. The mixture is cooled and 34.7 g (0.26 mole) of 2-piperidinoethyl chloride hydrochloride is added. After refluxing with stirring for 4 hours the mixture is cooled and 100 ml of water plus 10 ml of 50% NaOH solution are added. The mixture is stirred for 15 minutes and 100 ml of chloroform is added. The organic layer which separates is washed with 5% NaOH solution, then with water, dried over anhydrous magnesium sulfate, filtered and concentrated to a solid which is recrystallized from hexane to give 2,7-bis(2-bis(2-piperidinoethoxy)xanthene.

EXAMPLE 19

3,6-Bis(2-piperidinoethoxy)xanthone

To 54.5 g (0.239 mole) of 3,6-dihydroxyxanthen-9-one is added 240 ml of methanol and 29.0 g (0.717 mole) of sodium methoxide with stirring after which 700 ml of chlorobenzene is added. Methanol is distilled off until the reaction temperature reaches 130° C. After cooling the reaction mixture to less than about 100° C, 74.5 g (0.5 mole) of 2-piperidinoethylchloride is added and the reaction mixture refluxed for 4½ hours followed by the addition of 600 ml of water and 20 ml of 50% NaOH with stirring continued for ½ hour. The mixture is cooled and chloroform is added to completely dissolve the product. The chlorobenzene-chloroform layer is separated and the aqueous layer is extracted into chloroform. The combined organic layers are washed with water, dried over anhydrous magnesium sulfate and evaporated to give a dark brown oil which solidified upon cooling. The solid is dissolved in boiling ethanol, precipitated with water, cooled and filtered. The resulting solid is dried in vacuo and recrystallized from hexane to give 3,6-bis(2-piperidinoethoxy)xanthone, M.P. 134°-134.5° C.

EXAMPLE 20

2,7-Bis(2-piperidinoethoxy)anthraquinone dihydrochloride hemihydrate

With efficient stirring, 100 g (0.42 mole) of 2,7-dihydroxyanthraquinone is dissolved in 500-700 ml of about 10% potassium hydroxide solution. This solution is filtered and evaporated to dryness in a rotary evaporator. The reddish brown solid is dried in a vacuum over at 100° C, ground to a fine powder, then redried at 100° C. To a stirred suspension of 30 g of the powdered diphenoxide, containing about 24 g (0.075 mole) of the dipotassium salt of 2,7-dihydroxyanthraquinone, in 200 ml of xylene is heated to reflux and a small amount of water collected. A solution of 2-piperidinoethyl chloride in 100 ml of xylene, prepared from 53.3 g (0.29 mole) of 2-piperidinoethyl chloride hydrochloride, is added and the resulting mixture heated to reflux for about 24 hours. The mixture is poured into about 500 ml of water, and the solid which separates at the xylene/water interface is removed by filtration, washed with hot water and dried. This major portion of the free base is recrystallized from a mixture of hot methanol and chloroform, then dissolved in chloroform and acidified to Congo Red with ethereal HCl and diluted with ether. The precipitate is suspended in boiling methanol (12-20 ml per gram) and a small volume of water is added to effect solution. This solution is filtered, reduced about one-fourth in volume, diluted with additional methanol and chilled. The recrystallized dihydrochloride is filtered and dried in a vacuum oven at 100° C to give 2,7-bis(2-piperidino)anthrquinone dihydrochloride hemihydrate, M.P. 275°-277° C.

EXAMPLE 21

2,6-Bis(2-piperidinoethoxy)anthrquinone dihydrochloride

When in Example 20, 2,6-dihydroxyanthraquinone is substituted for 2,7-dihydroxyanthraquinone, 2,6-bis(2-piperidinoethoxy)anthraquinone dihydrochloride is obtained, M.P. 285-287° C.

EXAMPLE 22

2,8-Bis(3-piperidinopropylthio)dibenzothiophene dihydrochloride

When the appropriate molar equivalent amount of dibenzothiophene-2,8-dithiol is substituted for 2,8-dihydroxydibenzothiophene in the procedure described in Example 16, 2,8-bis(3-piperidinopropylthio)dibenzothiophene dihydrochloride is obtained.

EXAMPLE 23

2,7-Bis(4-piperidinobutylthio)fluorene dihydrochloride

When in the procedure in Example 13, fluorene-2,7-dithiol is substituted for 2,7-dihydroxyfluorene, 2,7-bis-(4-piperidinobutylthio)fluorene dihydrochloride is obtained.

EXAMPLE 24

2,8-Bis(3-piperidinopropylthio)dibenzofuran dihydrochloride

When in the procedure of Example 15, dibenzofuran-2,8-dithiol is substituted for 2,8-dihydroxyfuran, 2,8-bis(3-piperidinopropylthio)dibenzofuran dihydrochloride is obtained.

EXAMPLE 25

3,9-Bis[2-(4-methylpiperidino)acetyl]fluoranthene dihydrochloride

A solution of 3.9 g (0.011 mole) of 3,9-bis(-chloroacetyl)fluoranthene, 8.7 g (0.088 mole) of 4-methylpiperidine, 3.5 g of potassium iodode and 100 ml of butanone is refluxed with stirring for 16 hours then poured into water after which 500 ml of methylene chloride is added. The organic layer which separates is washed with a water-saturated sodium chloride solution, dried over magnesium sulfate and filtered. The filtrate is acidified with ethereal HCl and the solid which precipitates is recrystallized from methanol-butanone to give 3,9-bis[2-(4-methylpiperidino)acetyl]fluoranthene dihydrochloride, M.P. 228°-231° C.

EXAMPLE 26

3,9-Bis[4-(4-methylpiperidino)butyryl]fluoranthene dihydrochloride.

A solution of 20.6 g (0.05 mole) of 3,9-bis(4-chlorobutyryl 39.6 g (0.4 mole) of 4-methylpiperidine, 16.6 g of potassium iodide and 200 ml of butanone is refluxed with stirring for 24 hours then poured into water. The organic layer which separates is washed with a water-saturated sodium chloride solution, dried over magnesium sulfate, filtered and the filtrate acidified with ethereal HCl. The solid which precipitates is recrystallized three times from methanol-butanone to yield 3,9-bis[4-(4-methylpiperidino)butyryl]fluoranthene dihydrochloride, M.P. 254°-256° C.

EXAMPLE 27

3,9-Bis[4-(4-tert-butylpiperidino)butyryl]fluoranthene

In the procedure of Example 26 only substituting for 4-methylpiperidine, 33.9 g (0.24 mole) of 4-tert-butylpiperidine, the solid obtained on workup is recrystallized once from chloroform-acetone and once from methanolbutanone to yield 3,9-bis[4-(4-tert-butylpiperidino)-butyryl]fluoranthene, M.P. 150°-152° C.

EXAMPLE 28

2,7-Bis(4-piperidinobutyrylfluorene

A mixture of 18.8 g (0.05 mole) of 2,7-bis(4-chlorobutyryl)fluorene, prepared in Example 10, 34.0 g (0.4 mole) of piperidine, 16.6 g (0.1 mole) of potassium iodide in 200 ml of butanone is stirred and refluxed for three days. The reaction mixture is poured into 1000 ml of water, and the solid which is precipitated is filtered and recrystallized twice from chloroform-acetone to give 2,7-bis(4-piperidinobutyryl)fluorene, M.P. 157°–159° C.

EXAMPLE 29

2,7-Bis[4-(4-methylpiperidino)butyryl]fluorene

Following the procedure of Example 28 only substituting for piperidine, 39.6 g (0.4 mole) of 4-methylpiperidine, 2,7-bis[4-(4-methylpiperidino)butyryl]fluorene is obtained which is recrystallized twice from chloroform-acetone, M.P. 179.5°–181° C.

EXAMPLE 30

2,7-Bis[4-(4-benzylpiperidino)butyryl]fluorene

Following the procedure of Example 28 only substituting for piperidine, 70.0 g (0.4 mole) of 4-benzylpiperidine, 2,7-bis[4-(4-benzylpiperidino)butyryl]fluorene is obtained which is recrystallized from chloroform-acetone, M.P. 135°–137° C.

EXAMPLE 31

3,6-Bis(4-piperidinobutyryl)fluorene dihydrochloride

To a solution of 2.5 equivalents of 3-piperidinopropyl magnesium chloride, prepared from magnesium and 3-piperidinopropylchloride, in tetrahydrofuran, is added dropwise a solution of 1 equivalent of 3,6-dicyanofluorene dissolved in tetrahydrofuran. After the addition is complete the mixture is gently refluxed for 2 hours and stirred at room temperature for an additional 4 hours. The Grignard complex is decomposed by treating the reaction mixture dropwise with a saturated solution of ammonium chloride until the precipitation of magnesium salt is complete. The mixture is filtered and the filtrate is concentrated in vacuo. The residue is dissolved in dilute hydrochloric acid with warming then filtered. The aqueous solution is made alkaline and extracted with several portions of ether. The ether layers are combined, dried over magnesium sulfate and treated with ethereal HCl to give 3,6-bis(4-piperidinobutyryl)fluorene dihydrochloride, which is recrystallized from methanol-ethyl acetate.

EXAMPLE 32

2,7-Bis(4-piperidinobutyryl)fluoren-9-one

A solution of 9.0 g (0.019 mole) 2,7-bis(4-piperidinobutyryl)fluorene, 7.54 g (0.0253 mole) sodium dichromate and 300 ml of glacial acetic acid is stirred and refluxed for one hour. The reaction mixture is evaporated to semi-dryness and made basic using concentrated ammonium hydroxide. The solid which precipitates is filtered, washed with water and chromatographed on alumina using chloroform as the eluant. The solvent is removed from the fraction collected, leaving a solid residue which is recrystallized three times from chloroform-acetone to yield 2,7-bis(4-piperidinobutyryl)fluoren-9-one, M.P. 168°–170° C.

EXAMPLE 33

2,7-Bis[5-(4-benzylpiperidino)valeryl]fluoren-9-one

Following the procedure of Example 32 and substituting 17.0 g (0.025 mole) of 2,7-bis[5-(4-benzylpiperidino)valeryl]fluorene, the solid obtained is recrystallized twice from chloroform-acetone to yield 2,7-bis[5-(4-benzylpiperidino)valeryl]fluoren-9-one, M.P. 124°–126° C.

EXAMPLE 34

2,8-Bis(4-piperidinobutyryl)dibenzofuran

A mixture of 17.0 g (0.045 mole) of 2,8-bis(4-chlorobutyryl)dibenzofuran, 68.0 g (0.8 mole) of piperidine and 2.0 g of potassium iodide in 500 ml of butanone is heated at reflux for 72 hours then filtered. The filtrate is concentrated to one-half its original volume then diluted with 600 ml of water. The resulting semi-solid is purified by chromatography on neutral alumina using methylene chloride as the eluant. The solvent is removed from the fraction collected leaving a solid residue which is recrystallized from pentane to give 2,8-bis(4-piperidinobutyryl)dibenzofuran, M.P. 70°–71° C.

EXAMPLE 35

2,8-Bis[4-(4-methylpiperidino)butyryl]dibenzofuran

Following the procedure of Example 34, only substituting for piperidine, 79.2 g (0.8 mole) of 4-methylpiperidine and recrystallizing from ether-pentane 2,8-bis[4-(4-methylpiperidino)butyryl]dibenzofuran is obtained, M.P. 72°–73° C.

EXAMPLE 36

2,8-Bis(4-piperidinobutyryl)dibenzothiophene

A mixture of 28.0 g (0.072 mol) of 2,8-bis(4-chlorobutyryl)dibenzothiophene, 49.4 g (0.58 mole) of piperidine and 2.0 g of potassium iodide in 200 ml of tetrahydrofuran is heated at 125° C with stirring for 24 hours in a Parr general purpose bomb. The reaction mixture is cooled, filtered, and the filtrate is evaporated in vacuo leaving a residue which is washed with water and recrystallized twice from acetone to give 2,8-bis(4-piperidinobutyryl)dibenzothiophene, M.P. 93°–95° C.

EXAMPLE 37

2,8-Bis[4-(4-methylpiperidino)butyryl]dibenzothiophene

Following the procedure of Example 36, but substituting for piperidine, 57.42 g (0.58 mole) 4-methylpiperidine and recrystallizing from chloroform-acetone gives 2,8-bis-[4-(4-methylpiperidino)butyryl]dibenzothiophene, M.P. 136°–137.5° C.

EXAMPLE 38

N-Ethyl-3,6-bis(4-piperidinobutyryl)carbazole dihydrochloride hemihydrate

A mixture of 19.5 g (0.048 mole) of N-ethyl-3,6-bis-(4-chlorobutyryl)carbazole, 34.0 g (0.4 mole) of piperidine and 2.0 g of potassium iodide in 250 ml of p-dioxane is heated at reflux for 68 hours with stirring, then filtered. Upon cooling, the mixture is diluted with 500 ml of water, and the resulting semi-solid is dissolved in ether, washed repeatedly with water and dried over magnesium sulfate. The ethereal solution is treated with etheral HCl to give N-ethyl-3,6-bis(4-piperidinobutyryl)carbazole dihydrochloride hemihydrate, which is recrystallized from methanol-ethyl acetate, M.P. 138°–142° C.

EXAMPLE 39

3,6-Bis(4-piperidinobutyryl)carbazole

A solution of 15.0 g (0.04 mole) of 3,6-bis(4-chlorobutyryl)carbazole, 85.0 g (1.0 mole) of piperidine and 2.0 g of potassium iodide in 15 ml of tetrahydrofuran is heated at 110° C in a reaction bomb for 24 hours with stirring. Upon cooling, the reaction mixture is filtered and diluted with 700 ml of ice water. The resulting solid is washed with water, dried over magnesium sulfate and recrystallized from chloroform-petroleum ether (75°-90° C) and then from acetone to give 3,6-bis(4-piperidinobutyryl)carbazole, M.P. 171°-173° C.

EXAMPLE 40

2,7-Bis(4-piperidinobutyryl)xanthene

A mixture of 19.6 g (0.05 mole) of 2,7-bis(4-chlorobutyryl)xanthene, 34.0 g (0.4 mole) of piperidine, 16.6 g (0.1 mole) of potassium iodide and 200 ml of butanone is refluxed with stirring for 2½ days. The reaction mixture is poured into 1000 ml of water, and the solid which precipitates is filtered and recrystallized from methylene chloride-acetone then from acetone to give 2,7-bis(4-piperidinobutyryl)xanthene, M.P. 115°-117° C.

EXAMPLE 41

2,7-Bis(piperidinoacetyl)xanthene dihydrochloride

To a solution of 200 ml of piperidine in 500 ml of tetrahydrofuran are added 33.5 g (0.1 mole) of 2,7-bis(2-chloroacetyl)xanthene and 2 g of potassium iodide with warming. The reaction mixture is allowed to stand for 7 days, filtered and the filtrate evaporated to dryness, leaving a residue which is treated with dilute acid and filtered. The filtrate is made alkaline, and the resulting oily product is extracted with methylene chloride. The methylene chloride solution is acidified with ethereal HCl which gives an oily product that is recrystallized from methanol-diethyl ether then vacuum dried to give 2,7-bis(piperidinoacetyl)xanthene dihydrochloride, M.P. 260°-262° C.

EXAMPLE 42

2,7-Bis(4-piperidinobutyryl)xanthone

To a solution of 9.8 g (0.025 mole) of 2,7-bis(4-piperidinobutyryl)xanthene in 300 ml of glacial acetic acid is added 9.8 g (0.033 mole) of sodium dichromate over one-half hour. The mixture is stirred for 1½ hours, refluxed for 1 hours, then evaporated to near dryness, cooled, diluted with water and made alkaline with 28% NH4OH solution. The resulting solid is extracted with methylene chloride, chromatographed on alumina using methylene chloride as the eluant, recrystallized from heptane and dried under vacuum at 60° C to give the title compound, M.P. 93°-95° C.

EXAMPLE 43

2,7-Bis(5-piperidinovaleryl)thioxanthene

A mixture of 20 g of 2,7-bis(5-chlorovaleryl)thioxanthene, 2 g of potassium iodide, 70 ml of piperidine and 150 ml of tetrahydrofuran is heated in a Paar bomb at 100° C with stirring for 48 hours. Upon cooling, the solvent is evaporated, and the remaining material is poured into water then filtered. The residue is recrystallized several times from heptane to give 2,7-bis(5-piperidinovaleryl)thioxanthene, M.P. 98.5°-99.5° C.

EXAMPLE 44

2,7-Bis[5-(4-propylpiperidino)valeryl]thioxanthene

When in Example 43 an appropriate molar equivalent amount of 4-propylpiperidine is substituted for piperidine, 2,7-bis[5-(4-propylpiperidino)valeryl]thioxanthene is obtained.

EXAMPLE 45

2,8-Bis(5-piperidinovaleryl)phenoxathiin

A mixture of 35 g (0.08 mole) of 2,8-bis(5-chlorovaleryl)phenoxathiin, 2 g potassium iodide, 100 ml piperidine and 100 ml tetrahydrofuran is heated for 24 hours with stirring in a Parr bomb at 110° C. After cooling the mixture is filtered and washed with tetrahydrofuran, and the filtrate is evaporated to dryness. The residue is cooled and diluted with water. The mixture is extracted twice with ether, the ether extracts combined and filtered. The filtrate is evaporated to dryness, cooled and diluted with pentane followed by filtering off of the solid, washing with pentane and drying. The residue is recrystallized from isopropanol to yield 2,8-bis(5-piperidinovaleryl)phenoxathiin, M.P. 128.5°-129.5° C.

EXAMPLE 46

2,7-Bis(4-piperidinobutyryl)fluorene dihydrochloride

By the procedure of Example 28, 2,7-bis(4-piperidinobutyryl)fluorene is prepared and dissolved in a chloroformbutanone mixture. The resulting solution is acidified with ethereal HCl, and the solid precipitate recrystallized three times from methanol-butanone to give 2,7-bis(4-piperidinobutyryl)fluorene dihydrochloride, M.P. 286°-288° C.

EXAMPLE 47

2,7-Bis(5-piperidinovaleryl)xanthone

Following the procedure of Example 42, only substituting for 2,7-bis(4-piperidinobutyryl)xanthene, 25.8 g (0.05 mole) 2,7-bis(5-piperidinovaleryl)xanthene and using 600 ml of glacial acetic acid and 19.7 g (0.066 mole) sodium dichromate, the solid obtained is recrystallized from a benzene-heptane mixture to give the tital compound, M.P. 109°-110° C.

EXAMPLE 48

3,8-Bis(4-piperidinobutyryl)fluoranthene dihydrochloride

A solution of 2.5 equivalents of 3-piperidinopropylmagnesium chloride in tetrahydrofuran and 1 equivalent of 3,8-dicyanofluoranthene [N. Campbell et al, J. Chem. Soc., 2784 (1950)] dissolved in tetrahydrofuran are combined and refluxed for 2 hours followed by stirring for several hours at room temperature. The reaction mixture is treated with saturated ammonium chloride, and the organic layer is extracted into chloroform and treated with dilute HCl. The chloroform is distilled off, and the aqueous solution is filtered, cooled, made alkaline and extracted with several portions of ether. The ether layers are combined, dried over magnesium sulfate and treated with ethereal HCl. The precipitate is recrystallized from methanol-ethyl acetate to give 3,8-bis(4-piperidinobutyryl)fluoranthene dihydrochloride.

EXAMPLE 49

3,9-Bis[5-(4-benzylpiperidino)valeryl]fluoranthene

Following the procedure of Example 26 with the exception that 13.2 g (0.03 mole) of 3,9-bis(5-chlorovaleryl)fluoranthene, prepared from fluoranthene and 5-chlorovalerylchloride, and 42.0 g (0.24 mole) of 4-benzylpiperidine are used, the solid obtained on workup is recrystallized twice from chloroform-acetone yielding 3,9-bis[5-(4-benzylpiperidino)valeryl]fluoranthene, M.P. 126.5°–128° C.

EXAMPLE 50

2,7-Bis(4-chlorobutyryl)fluorene

To a solution of 23.6 g (0.142 mole) of fluorene and 50.0 g (0.35 mole) of 4-chlorobutyryl chloride in 1500 ml of methylene chloride chilled to −20° C is added 39.8 g (0.298 mole) of aluminum chloride with rapid stirring. The reaction mixture is refluxed four hours, stirred at room temperature for 16 hours, then poured onto ice/conc. HCl. The organic layer is separated, washed with saturated sodium bicarbonate solution and dried over magnesium sulfate. After filtration, the methylene chloride solution is evaporated to dryness and the solid residue recrystallized from acetone to yield 2,7-bis(4-chlorobutyryl)fluorene, M.P. 172°–175° C.

EXAMPLE 51

When in the procedure of Example 50 the polycyclic aromatic compounds and the haloalkanoyl halides listed below are employed the respective products listed below are obtained:

| Polycyclic Aromatic | Haloalkanoyl Halide | Product |
| --- | --- | --- |
| fluorene | 4-chlorovaleryl chloride | 2,7-bis(5-chlorovaleryl)fluorene, M.P. 124–125° C. |
| N-ethylcarbazole | 4-chlorobutyryl chloride | 3,6-bis(4-chlorobutyryl)-N-ethyl-carbazole, M.P. 106–108° C. |
| N-ethylcarbazole | 5-chlorovaleryl chloride | 3,6-bis(5-chlorovaleryl)-N-ethyl-carbazole, M.P. 94–95° C. |
| carbazole | 4-chlorobutyryl chloride | 3,6-bis(4-chlorobutyryl)carbazole, M.P. 195–198° C. |
| dibenzofuran | 4-chlorobutyryl chloride | 2,8-bis(4-chlorobutyryl)dibenzofuran, M.P. 102–104° C. |
| dibenzofuran | 5-chlorovaleryl chloride | 2,8-bis(5-chlorovaleryl)dibenzofuran. |
| dibenzothiophene | 4-chlorobutyryl chloride | 2,8-bis(4-chlorobutyryl)dibenzothiophene, M.P. 131–133° C. |
| phenoxathiin | 5-chlorovaleryl chloride | 2,7-bis(5-chlorovaleryl)phenoxathiin, M.P. 121–122° C and 2,8-bis(5-chlorovaleryl)phenoxathiin, M.P. 130–1° C. |
| thioxanthene | 5-chlorovaleryl chloride | 2,7-bis(5-chlorovaleryl)thioxanthene |
| thioxanthene | 4-chlorobutyryl chloride | 2,7-bis(4-chlorobutyryl)thioxanthene, M.P. 115–116° C. |
| xanthene | 4-chlorobutyryl chloride | 2,7-bis(4-chlorobutyryl)xanthene, M.P. 131–132° C. |
| xanthene | 2-chloroacetyl chloride | 2,7-bis(2-chloroacetyl)xanthene, M.P. 200–201° C. |
| xanthene | 5-chlorovaleryl chloride | 2,7-bis(5-chlorovaleryl)xanthene. |
| fluoranthene | 2-chloroacetyl chloride | 3,9-bis(2-chloroacetyl)fluoranthene |
| fluoranthene | 4-chlorobutyryl chloride | 3,9-bis(4-chlorobutyryl)fluoranthene |
| dibenzofuran | 4-chloro-2-methyl-butyryl chloride | 2,8-bis(4-chloro-2-methylbutyryl)-dibenzofuran |

EXAMPLE 52

2,8-Dicyanodibenzothiophene

To a mixture of one equivalent of 2,8-dibenzothiophenedicarboxylic acid, prepared by a Friedel-Crafts reaction between dibenzothiophene and oxalyl chloride, and 2.2 equivalents of p-toluenesulfonamide is added 4.5 equivalents of phosphorous pentachloride. After the initial reaction subsides the reaction mixture is heated to 200° C to remove the volatile secondary products. The solid residue remaining is cooled and treated with pyridine and water. The suspension is filtered, washed with water and suspended in a dilute sodium hydroxide solution followed by filtration and washing with water to give 2,8-dicyanodibenzothiophene which is recrystallized from a dimethylformamide-water combination. In like manner 2,6-dicyanodibenzothiophene is prepared.

EXAMPLE 53

When in the procedure of Example 52, 4,6-dibenzofurandicarboxylic acid [H. Gilman and R. Young, J. Am. Chem. Soc. 57, 1121 (1935)] or 1,7-fluorenedicarboxylic acid [Bamberger and Hooker, Ann. 229, 151, 154, 161 (1885)] is substituted for 2,8-dibenzothiophenedicarboxylic acid, the following respective products are obtained:
  4,6-dicyanodibenzofuran, and
  1,7-dicyanofluorene.

EXAMPLE 54

2,5-Dicyanofluorene

To one equivalent of 2,5-diaminofluorene [G. Morgan and R. Thomason, J. Chem. Soc., 2695 (1926)] dissolved in dilute hydrochloric acid and cooled to 0° C is added 2.2 equivalents of sodium nitrile, and the mixture is cautiously neutralized with sodium carbonate. This mixture is added portionwise to a cold solution of 2.5 equivalents of cuprous cyanide with stirring to give 2,5-dicyanofluorene which is purified from a dimethylformamide-water combination. In like manner 2,7- and 3,6-dicyanofluorene may be prepared.

EXAMPLE 55

When in the procedure of Example 54, 3,7-diaminodibenzothiophene [R. Brown et al., J. Am. Chem. Soc. 74, 1165 (1952)] or 3,8-diaminodibenzofuran [M. Culinane, J. Chem. Soc. 2365 (1932)] is substituted for 2,5-diamino-fluorene, the following respective products are obtained:
  3,7-dicyanodibenzothiophene, and
  3,8-dicyanodibenzofuran.

Additional examples for the preparation of bis-piperidinoalkanoyl derivatives of fluoranthene are set forth in Great Britain Pat. No. 1,304,651, of fluorene and fluoren-9-one are set forth in Great Britain Pat. No. 1,286,755, of dibenzofuran are set forth in Belgian Pat. No. 772,582, of dibenzothiophene are set forth in Great Britain Pat. No. 1,292,567, of thioxanthene are set forth in Great Britain Pat. No. 1,312,534, of xanthene and xanthone are set forth in Belgian Pat. No. 776,535, and of phenoxathiin are set forth in W. German Pat. No. 2,231,067, and the appropriate examples disclosed therein are incorporated herein by reference thereto.

The following examples are illustrative of pharmaceutical preparations containing compounds of general Formula I as active ingredients.

EXAMPLE 56

An illustrative composition for tablets is as follows:

|   |   | Per Tablet |
|---|---|---|
| (a) | bis(3-piperidinopropyl)fluorene-2,7-dicarboxylate dihydrochloride | 100.0 mg |
| (b) | wheat starch | 15.0 mg |
| (c) | lactose | 33.5 mg |
| (d) | magnesium stearate | 1.5 mg |

A portion of the wheat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 57

An illustrative composition for a parenteral injection is the following wherein the quantities are on a weight to volume bases.

|   |   | amount |
|---|---|---|
| (a) | 3,6-bis(2-piperidinoethoxy)-xanthone | 100.0 mg |
| (b) | sodium chloride | q.s. |
| (c) | water for injection to make | 10.0 ml |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 58

An illustrative composition for hard gelatin capsules is as follows:

|   |   | Per Capsule |
|---|---|---|
| (a) | 3,9-bis(4-methylpiperidinoacetyl)-fluoranthene dihydrochloride | 200.0 mg |
| (b) | talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 59

An illustrative composition for pills is as follows:

|   |   | Per Pill |
|---|---|---|
| (a) | 2,8-bis(4-piperdinobutyryl)dibenzothiophene | 200 mg |
| (b) | corn starch | 130 mg |
| (c) | liquid glucose | 20 ml |

The pills are prepared by blending the active ingredient (a) and the corn starch then adding the liquid glucose with thorough kneading to form a plastic mass from which the pills are cut and formed.

I claim:

1. A method of treating conditions of delayed hypersensitivity which comprises administering to a patient in need thereof a compound of the formula

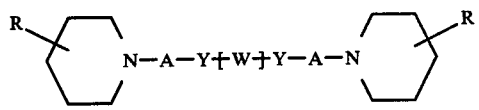

wherein [W] is an aromatic polycyclic nucleus selected from the group consisting of dibenzofuran, dibenzothiophene, carbazole, N-(lower)alkylcarbazole, xanthene, xanthone, thioxanthene, and phenoxathiin; each Y is carbonyloxy, carbonylthio, oxygen, divalent sulfur, or carbonyl with the proviso that when Y is carbonyloxy or carbonylthio, [W] is other than thioxanthene or phenoxathiin, and when Y is oxygen or divalent sulfur, [W] is other than thioxanthene or phenoxathiin; A is a straight or branched alkylene chain of from 1 to 6 carbon atoms with the proviso that when Y is carbonyloxy or carbonylthio, A contains from 2 to 6 carbon atoms; R is hydrogen, a straight or branched lower alkyl group of from 1 to 4 carbon atoms, phenyl or benzyl; or a pharmaceutically acceptable acid addition salt thereof, in an amount effective to suppress delayed hypersensitivity.

2. The method of claim 1 wherein each Y is carbonyloxy or carbonylthio.

3. The method of claim 2 wherein [W] is dibenzofuran, dibenzothiophene, carbazole, N-(lower)alkylcarbazole, xanthene or xanthone.

4. The method of claim 1 wherein each Y is oxygen or divalent sulfur.

5. The method of claim 4 wherein [W] is dibenzofuran, dibenzothiophene, carbazole, N-(lower)alkylcarbazole, xanthene or xanthone.

6. The method of claim 5 wherein the compound is 2,8-bis(3-piperidinopropoxy)dibenzofuran or a pharmaceutically acceptable acid addition salt thereof.

7. The method of claim 1 wherein each Y is carbonyl.

8. The method of claim 7 wherein [W] is dibenzofuran, dibenzothiophene, carbazole, N-(lower)alkylcarbazole, xanthene, xanthone, thioxanthene or phenoxathiin.

* * * * *

UNITED STATES PATENT AND TRADEMARK OFFICE
CERTIFICATE OF CORRECTION

PATENT NO. : 4,041,165

DATED : August 9, 1977

INVENTOR(S) : Irving Shemano

Page 1 of 2

It is certified that error appears in the above-identified patent and that said Letters Patent are hereby corrected as shown below:

Column 1, line 45 ...ketoe... should read --ketone--. Column 2, line 45 ...dibenzothiphene... should read --dibenzothiophene--. Column 4, lines 54-55 ...may represent in the may represent in the compounds... should read --may represent in the compounds--; line 67 ...(4-piperidinobutyoxy)... should read --(4-piperidinobutoxy)--. Column 5, line 4 ...(5-piperidinoopentoxy)... should read --(5-piperidinopentoxy)--; line 10 ...dibenzothiphene... should read --dibenzothiophene--; line 27 ...phenylpiperidono)... should read --phenylpiperidino)--; line 54 ...or suitable... should read --are suitable--. Column 7, line 39 ...R represents hydrogen, lower alkyl of from 1 to 4 carbon atoms; R represents hydrogen, lower alkyl of from 1 to 4 carbon atoms, phenyl... should read --R represents hydrogen, lower alkyl of from 1 to 4 carbon atoms, phenyl--. Column 8, line 51 ...fluorene... should read --fluorenone--. Column 9, line 40 ...Hal-A-Hac... should read --Hal-A-Hal--. Column 14, line 18 ...to reflux... should read --at reflux--; line 44 ...erystalline... should read --crystalline--; line 55 ...oxofluorene:2,7-... should read --oxofluorene-2,7- --. Column 18, line 20 ...2,7 bis... should read --2,8 bis--; line 57 ...2,7-bis(2-bis(2-... should read --2,7-bis(2- --. Column 19, line 24 ...over... should read --oven--; line 48 ...2,7-bis(2-piperidino)-anthrquinone... should read --2,7-bis(2-piperidinoethoxy)-anthraquinone--; line 53 ...anthrquinone... should read --anthraquinone--. Column 20, line 14 ...dihydroxyfuran... should read --dihydroxydibenzofuran--; line 23 ...iodode... should read --iodide---; line 39 ...(4-chlorobutyryl .. should read --(4-chlorobutyryl)fluoranthene--; line 60 ...(4-piperidinobutyryl fluorene... should read --(4-piperidinobutyryl)fluorene--. Column 21, line 23 ...(4-piperidinobutyryl fluorene... should read --(4-piperidinobutyryl)fluorene--. Column 22, line 27 ...mol... should

UNITED STATES PATENT AND TRADEMARK OFFICE
CERTIFICATE OF CORRECTION

PATENT NO. : 4,041,165

DATED : August 9, 1977

INVENTOR(S) : Irving Shemano

It is certified that error appears in the above-identified patent and that said Letters Patent are hereby corrected as shown below:

read --mole--. Column 23, line 45 ...1 hours... should read --1 hour--. Column 24, line 39 ...tital... should read --title--. Column 25, 8th listing, 3rd Column ...130-3/8°C... should read --130-132°C--.

Signed and Sealed this

Eleventh Day of July 1978

[SEAL]

Attest:

RUTH C. MASON
*Attesting Officer*

DONALD W. BANNER
*Commissioner of Patents and Trademarks*